United States Patent [19]

Kondo et al.

[11] Patent Number: 4,524,373
[45] Date of Patent: Jun. 18, 1985

[54] FLUORAN DERIVATIVES AS NEW COMPOUNDS, PROCESS FOR PREPARING THE SAME AND RECORDING SYSTEM UTILIZING THE SAME AS COLORLESS CHROMOGENIC MATERIAL

[75] Inventors: Mitsuru Kondo, Hyogo; Hiroshi Iwasaki, Kawanishi; Nobuo Kanda, Osaka; Masayuki Omatsu; Haruo Omura, both of Motomachi, all of Japan

[73] Assignee: Kanzaki Paper Manufacturing Co., Ltd., Tokyo, Japan

[21] Appl. No.: 467,286

[22] Filed: Feb. 17, 1983

[30] Foreign Application Priority Data

| Feb. 24, 1982 | [JP] | Japan | 57-30058 |
| Feb. 26, 1982 | [JP] | Japan | 57-31465 |
| Feb. 27, 1982 | [JP] | Japan | 57-31543 |
| Apr. 16, 1982 | [JP] | Japan | 57-64231 |
| Apr. 21, 1982 | [JP] | Japan | 57-67632 |
| May 6, 1982 | [JP] | Japan | 57-76972 |
| Oct. 8, 1982 | [JP] | Japan | 57-178144 |

[51] Int. Cl.$^3$ .............. B41M 5/18; S41M 5/22
[52] U.S. Cl. .............. 346/221; 346/217; 427/151
[58] Field of Search ........ 282/27.5; 427/151; 428/320.4, 320.6, 320.8, 411, 488, 537, 913, 914, 411.1, 488.1, 537.5; 549/226; 346/217, 221

[56] References Cited

U.S. PATENT DOCUMENTS

| 3,681,390 | 8/1972 | Lin | 282/27.5 |
| 3,746,562 | 7/1973 | Lin | 282/27.5 |
| 3,764,369 | 10/1973 | Hoover et al. | 282/27.5 |
| 3,769,302 | 10/1973 | Hoover et al. | 282/27.5 |
| 3,920,510 | 11/1975 | Hatano et al. | 282/27.5 |

FOREIGN PATENT DOCUMENTS

| 2905825 | 8/1979 | Fed. Rep. of Germany | 346/221 |
| 116685 | 7/1982 | Japan | 346/221 |
| 153050 | 9/1982 | Japan | 346/221 |

Primary Examiner—Bruce H. Hess
Attorney, Agent, or Firm—Fisher, Christen & Sabol

[57] ABSTRACT

A new fluoran derivative useful as a colorless chromogenic material has the general formula:

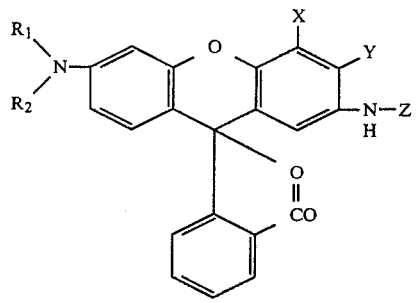

wherein $R_1$, $R_2$, X, Y and Z have the same meaning as defined hereinbefore.

3 Claims, No Drawings

FLUORAN DERIVATIVES AS NEW COMPOUNDS, PROCESS FOR PREPARING THE SAME AND RECORDING SYSTEM UTILIZING THE SAME AS COLORLESS CHROMOGENIC MATERIAL

BACKGROUND OF THE INVENTION

This invention relates to fluoran derivatives as new compounds useful as colorless chromogenic materials, a new process for preparing the same, and a new recording system utilizing the same.

There are known various kinds of recording systems utilizing the colorforming reaction between a colorless chromogenic material and an electron accepting acidic reactant material by the medium of mechanical, heat, electric or light energy. Among them there are included a pressure sensitive record sheet, a heat sensitive record sheet, an electrothermal record sheet, an ultrasonic record sheet, an electron beam record sheet, an electrostatic record sheet and a photosensitive record sheet. The colorless chromogenic materials of these kinds also find their usefulness in photosensitive printing compositions, typewriter ribbons, ball-point pen ink, crayon and stamp ink.

In the recording system utilizing the color forming reaction between a colorless chromatogenic material (hereinafter referred to as "color former") and an electron accepting acidic reactant material (hereinafter referred to as "acceptor"), images of various colors can be developed by using different kinds of color formers. There is now an increased demand for record materials which develop black color images which can be reproducible for copies. Theoretically images of substantially black color can be obtained by using a mixture of various color formers which develop the respective different colors, e.g., red, blue, yellow and green. The utilization of a mixture of different color formers for obtaining a black color has, however, a disadvantage that the once developed black color images cannot be maintained for a long time because different color formers have different color developing speeds and different light and moisture resistances. Some attempts have been made to obtain images of substantially black color through the utilization of a single color former. However, there has yet been found no single color former which can develop substantially black color images without sacrificing all the stability of the color former before color developing, color developing speed, color density, color tone and stability of the color images developed and its production cost.

The primary object of the invention is to provide novel fluoran derivatives useful as color formers for use in various recording systems.

Another object of the invention is to provide novel color formers for use in recording systems in which the color images when developed therefrom assume a substantially deep-black color and have a good light resistance.

A further object of the invention is to provide novel color formers for use in heat sensitive recording systems in which substantially no fogging occurs on the record materials to which they are applied.

A still further object of the invention is to provide novel color formers for use in recording systems which have a good and instant color developability.

One of other objects of the invention is to provide a novel process for preparing fluoran derivatives of the kind described above.

It is also included among the objects of the invention to provide an improved recording system in which a fluoran derivative as a new compound is used as a color former and the color images when developed therefrom have a good light resistance and assume a substantially deep-black color which is suitable for reproduction of copies.

Other objects and advantages of the invention will become apparent from the following description.

SUMMARY OF THE INVENTION

The novel fluoran derivatives according to the invention have the general formula:

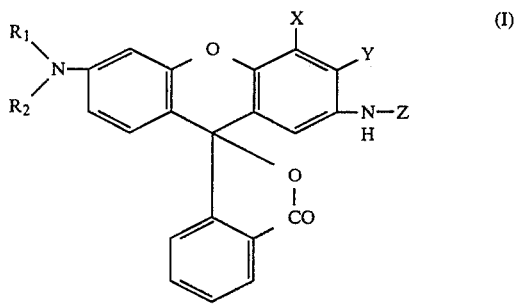

wherein
Z is $-CH_2COOCH_2CH=CH_2$,

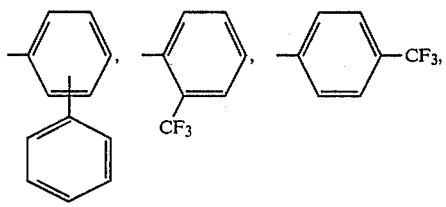

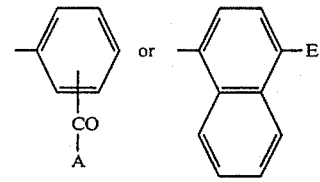

wherein A is an alkyl having 1 to 18 carbon atoms or an aryl which may be substituted by at least one substituent selected from the group consisting of halogen atoms and alkyls having 1 to 4 carbon atoms, E is hydrogen or

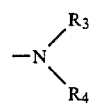

wherein each $R_3$ and $R_4$ is hydrogen, an alkyl having 1 to 4 carbon atoms or phenyl;
each $R_1$ and $R_2$ is an alkyl having 1 to 12 carbon atoms, an aralkyl having 7 to 9 carbon atoms, cyclohexyl or phenyl which may be substituted by at least one substituent selected from the group consisting of halogen atoms and alkyls having 1 to 4 carbon atoms, or both of $R_1$ and $R_2$ together with the adjacent nitrogen may form a heterocyclic ring; X is hydrogen, halogen atom, an alkyl having 1 to 4 carbon atoms or an alkoxyl having 1 to 2 carbon atoms; and Y is hydrogen, halogen atom or an alkyl having 1 to 4 carbon atoms; however,
when
Z is —$CH_2COOCH_2CH=CH_2$ or

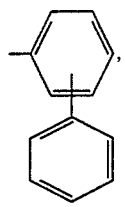

each $R_1$ and $R_2$ is an alkyl having 1 to 12 carbon atoms or an aralkyl having 7 to 9 carbon atoms,
when
Z is

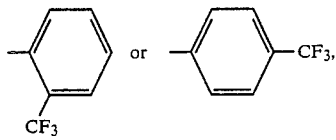

each $R_1$ and $R_2$ is an alkyl having 1 to 4 carbon atoms, X is hydrogen and Y is hydrogen or methyl,
when
Z is

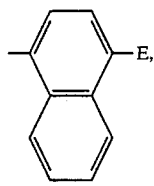

each $R_1$ and $R_2$ is an alkyl having 1 to 12 carbon atoms or an aralkyl having 7 to 9 carbon atoms, and, at least one of X and Y is selected from the before-mentioned substituents other than hydrogen, and
when
Z is

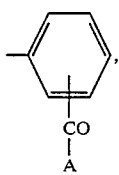

A is an alkyl having 1 to 18 carbon atoms
and each $R_1$ and $R_2$ is an alkyl having 1 to 12 carbon atoms or an aralkyl having 7 to 9 carbon atoms,
at least one of X and Y is selected from the before-mentioned substituents other than hydrogen.

The fluoran derivatives having the above general formula (I) can be used as color formers for use in various recording systems including a pressure sensitive recording system and a heat sensitive recording system. The compounds according to the invention can produce a color of substantially deep-black upon contact with an electron accepting acidic reactant material. The color images produced has a good light resistance and can maintain its clear color tone initially produced for a long time.

DETAILED DESCRIPTION OF THE INVENTION

The compounds represented by the formula (I) may preferably be prepared by reacting 2-(2-hydroxy-4-amino)benzoylbenzoic acid derivative (benzophenone derivative) represented by the following formula:

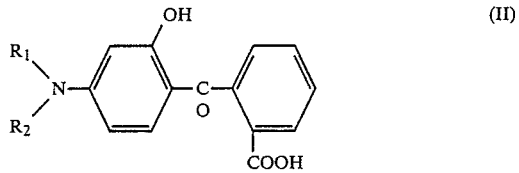

wherein $R_1$ and $R_2$ are the same as above defined, respectively, with p-aminophenol derivative represented by the following formula:

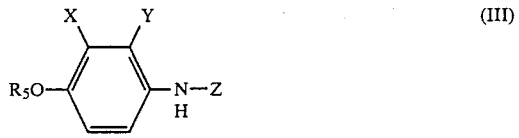

wherein Z, X and Y are the same as above defined, respectively, and $R_5$ is hydrogen, methyl or ethyl, in the presence of a condensing agent.

The compounds represented by the formula (II) may preferably be prepared by making m-aminophenol derivatives represented by the general formula (IV) react with phthalic anhydride represented by the general formula (V) as follows:

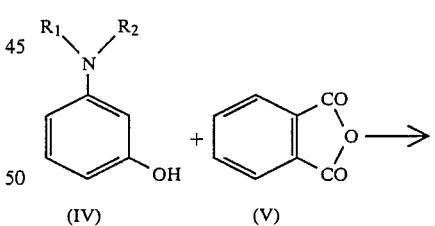

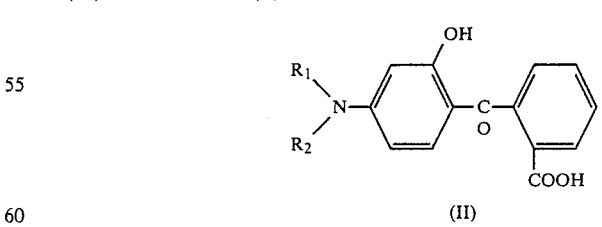

wherein $R_1$ and $R_2$ are the same as defined before.

The condensing agent used for the reaction between the derivative represented by the general formula (II) and the derivatives represented by the general formula (III) may preferably be at least one Friedel-Crafts Type Catalyst such as sulfuric acid; phosphorus pentoxide; phosphoric acid; polyphosphoric acid; anhydrous metal halide such as anhydrous tin chloride, anhydrous zinc chloride, anhydrous aluminum chloride, anhydrous tin bromide, anhydrous zinc bromide, anhydrous aluminum bromide and anhydrous iron bromide; phosphorus trichloride; phosphorus tribromide; phosphorus pentachloride; phosphorus pentabromide; anhydrous boron trifluoride; and hydrofluoric acid. The most preferred condensing agent is sulfuric acid.

Among useful solvents in the above reaction, there are included carbon disulfide, monochlorobenzene, trichlorobenzene, nitrobenzene, nitromethane and nitroethane. Sulfuric acid which is the most preferred condensing agent also functions as a good solvent.

In the reaction of the compound represented by the formula (II) with the compound represented by the formula (III) in the presence of the above mentioned condensing agent, if $R_5$ is methyl or ethyl in the compound represented by the formula (III), there are occasionally produced triphenylmethane derivative represented by the following formula:

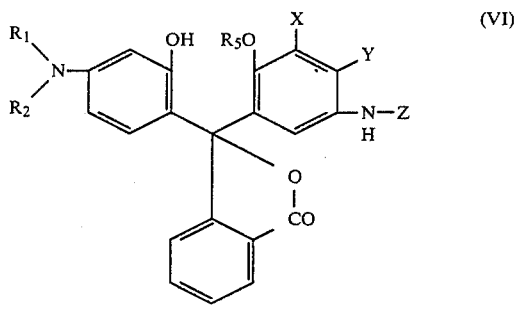

(VI)

wherein $R_5$ is methyl or ethyl and Z, $R_1$, $R_2$, X and Y are the same as above defined, respectively.

The above derivatives represented by the formula (VI) can be changed to the compounds represented by the formula (I) by taking the following steps:

preparing an aqueous system including the derivatives represented by the formula (VI);

adjusting the pH of the aqueous system to higher than 9.0, preferably to 9.5 to 12.5 by addition of basic materials such as NaOH, KOH and the like; and then heating the aqueous system to a temperature of 50° C. to 100° C.

In order to increase the yield of the compounds represented by the formula (I) in above manner an organic solvent such as acetone, benzene, toluene or xylene may preferably be added to the aqueous system including the derivatives represented by the formula (VI). Hydrophobic organic solvents such as benzene, toluene and xylene are especially advantageous to effectively prevent by-products from being formed.

In one aspect of the invention the novel fluoran derivatives are represented by the general formula:

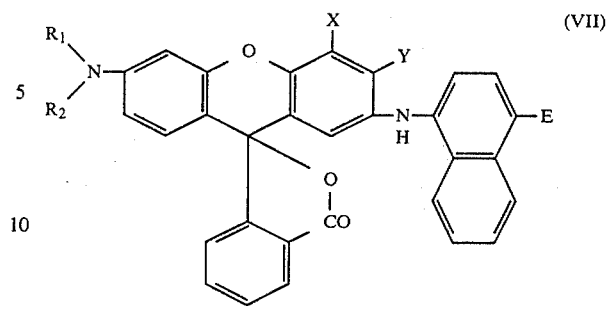

(VII)

wherein each $R_1$ and $R_2$ is an alkyl having 1 to 12 carbon atoms or an aralkyl having 7 to 9 carbon atoms, X is hydrogen, halogen atom, an alkyl having 1 to 4 carbon atoms or an alkoxyl having 1 to 2 carbon atoms, and Y is hydrogen, halogen atom or an alkyl having 1 to 4 carbon atoms, however, at least one of X and Y is selected from the before-mentioned substituents other than hydrogen, and E is hydrogen or

wherein each $R_3$ and $R_4$ is hydrogen, an alkyl having 1 to 4 carbon atoms or phenyl.

The compounds represented by the above formula (VII) are colorless or substantially colorless and stable materials. A deep black or reddish black color is developed from those compounds upon contact with acceptors. The color images produced with use of those compounds have a good light resistance and can maintain its color tone initially produced for a long time.

In another aspect of the invention the novel fluoran derivatives are represented by the general formula:

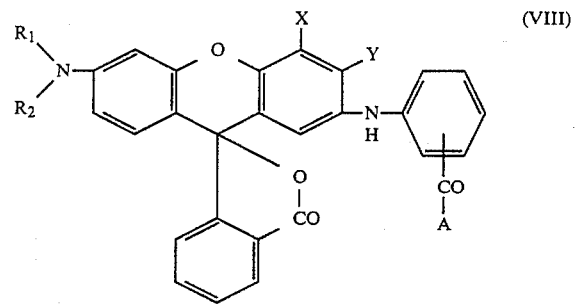

(VIII)

wherein each $R_1$ and $R_2$ is an alkyl having 1 to 12 carbon atoms or an aralkyl having 7 to 9 carbon atoms, X is hydrogen, halogen atom, an alkyl having 1 to 4 carbon atoms or an alkoxyl having 1 to 2 carbon atoms, and Y is hydrogen, halogen atom or an alkyl having 1 to 4 carbon atoms, however, at least one of X and Y is selected from the before-mentioned substituents other than hydrogen, and A is an alkyl having 1 to 18 carbon atoms or an aryl which may be substituted by at least one substituent selected from the group consisting of halogen atoms and alkyls having 1 to 4 carbon atoms.

The compounds represented by the above formula (VIII) are colorless or substantially colorless and stable materials. A deep black, reddish black or greenish black color is developed upon contact with acceptors. The color images produced with use of those compounds have a good light resistance and can maintain its color tone initially produced for a long time. The reason why these good effects are obtained is considered due to the fact that the compounds represented by the formula (VIII) have an acyl group. The pressure-sensitive record materials utilizing those compounds show an instant color developability. The heat-sensitive record materials utilizing those compounds have a good color developability while substantially no fogging is caused thereon.

In a further aspect of the invention the novel fluoran derivatives are represented by the general formula:

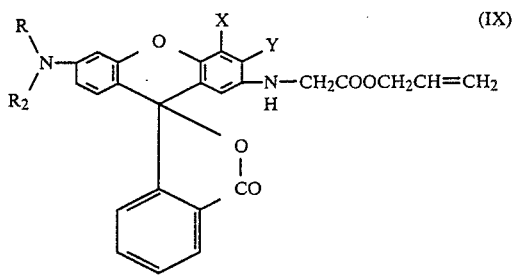

(IX)

wherein each $R_1$ and $R_2$ is an alkyl having 1 to 12 carbon atoms or an aralkyl having 7 to 9 carbon atoms, X is hydrogen, halogen atom, an alkyl having 1 to 4 carbon atoms or an alkoxyl having 1 to 2 carbon atoms, and Y is hydrogen, halogen atom or an alkyl having 1 to 4 carbon atoms.

The compounds represented by the above formula (IX) are colorless or substantially colorless and stable materials. A deep black or reddish black color is developed therefrom upon contact with acceptors. They have a good light resistance and can maintain its color tone initially produced for a long time. The heat-sensitive record materials utilizing those compounds show substantially no fogging while they have a good color developability.

In a still another aspect of the invention the novel fluoran derivatives are represented by the general formula:

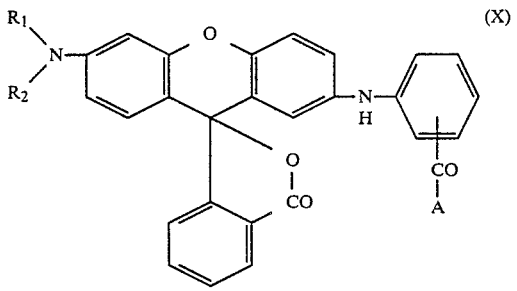

(X)

wherein each $R_1$ and $R_2$ is an alkyl having 1 to 12 carbon atoms or an aralkyl having 7 to 9 carbon atoms and A is an aryl which may be substituted by at least one substituent selected from the group consisting of halogen atoms and alkyls having 1 to 4 carbon atoms.

The compounds represented by the above formual (X) are colorless or substantially colorless and stable materials. A deep black, reddish black or greenish black color is produced therefrom upon contact with acceptors. The color images produced with use of those compounds have a good light resistance and can maintain its color tone initially produced for a long time. The reason why these good effects are obtained is considered due to the fact that the compounds represented by the formula (X) have an acyl group. The pressure-sensitive record materials utilizing those compounds show an instant color developability. The heat-sensitive record materials utilizing those compounds have a good color developability while substantially no fogging is caused thereon.

In one of other aspects of the invention the novel fluoran derivatives are represented by the general formula:

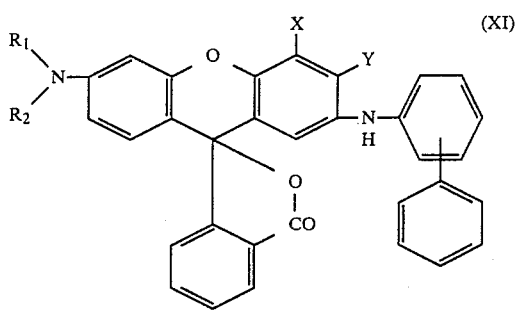

(XI)

wherein each $R_1$ and $R_2$ is an alkyl having 1 to 12 carbon atoms or an aralkyl having 7 to 9 carbon atoms, X is hydrogen, halogen atom, an alkyl having 1 to 4 carbon atoms or an alkoxyl having 1 to 2 carbon atoms, and Y is hydrogen, halogen atom or an alkyl having 1 to 4 carbon atoms.

The compounds represented by the above formula (XI) are colorless or substantially colorless and stable materials. A deep black or reddish black color is developed therefrom upon contact with acceptors. They have a good light resistance and can maintain its color tone initially produced for a long time. The heat-sensitive record materials utilizing those compounds show substantially no fogging while they have a good color developability.

In a still further aspect of the invention the novel fluoran derivatives are represented by the general formula:

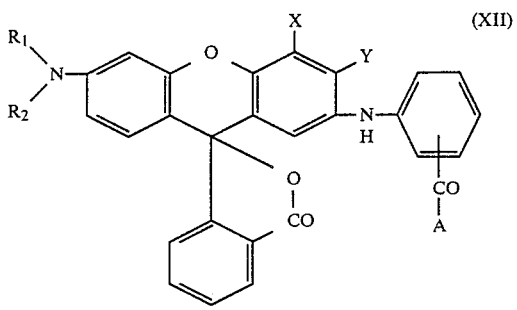

(XII)

wherein $R_1$ is cyclohexyl or phenyl which may be substituted by at least one substituent selected from the group consisting of halogen atoms and alkyls having 1 to 4 carbon atoms, $R_2$ is an alkyl having 1 to 4 carbon atoms, or both of $R_1$ and $R_2$ together with the adjacent nitrogen may form a heterocyclic ring, X is hydrogen, halogen atom, an alkyl having 1 to 4 carbon atoms or an alkoxyl having 1 to 2 carbon atoms, Y is hydrogen, halogen atom or an alkyl having 1 to 4 carbon atoms, and A is an alkyl having 1 to 18 carbon atoms or an aryl which may be substituted by at least one substituent selected from the group consisting of halogen atoms and alkyls having 1 to 4 carbon atoms.

The compounds represented by the above formula (XII) are colorless or substantially colorless and stable materials. A deep black, reddish black or greenish black color is developed upon contact with acceptors. The color images produced with use of those compounds have a good light resistance and can maintain its color tone initially produced for a long time. The reason why these good effects are obtained is considered due to the fact that the compounds represented by the formula (XII) have an acyl group. The pressure-sensitive record materials utilizing those compounds show an instant color developability. The heat-sensitive record materials utilizing those compounds have a good clear developability while substantially no fogging is caused thereon.

In the other aspect of the invention the novel fluoran derivatives are represented by the general formula:

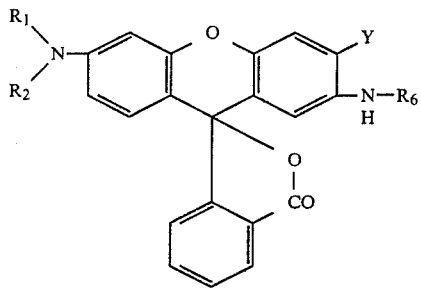

(XIII)

wherein each $R_1$ and $R_2$ is an alkyl having 1 to 4 carbon atoms, $R_6$ is

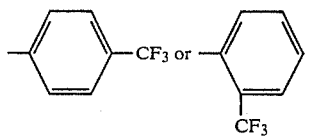

and Y is hydrogen or methyl.

The compounds represented by the above formula (XIII) are colorless or substantially colorless and stable materials. A deep black, reddish black or greenish black color is developed upon contact with acceptors. The color images produced with use of those compounds have a good light resistance and can maintain its color tone initially produced for a long time. The pressure-sensitive record materials utilizing those compounds show an instant color developability. The heat-sensitive record materials utilizing those compounds have a good color developability while substantially no fogging is caused thereon.

The fluoran derivatives represented by the formula (IX) may also be prepared by any of the following manners:

(a) making 3-N,N-disubstituted-amino-7-amino fluoran derivative represented by the general formula:

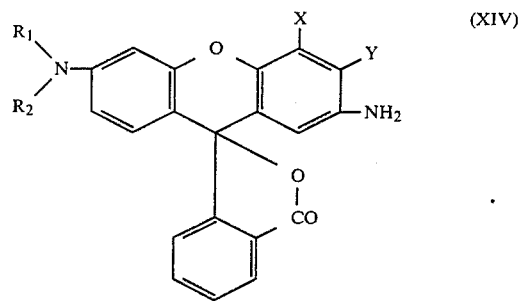

(XIV)

wherein $R_1$, $R_2$, X and Y are the same as described above react with the compound represented by the general formula:

$$Q_1-CH_2-COOCH_2CH=CH_2 \qquad (XV)$$

wherein $Q_1$ is halogen atom; or, (b) allyl-esterifying 3-N,N-disubstituted-amino-7-carboxymethylamino fluoran derivative represented by the general formula:

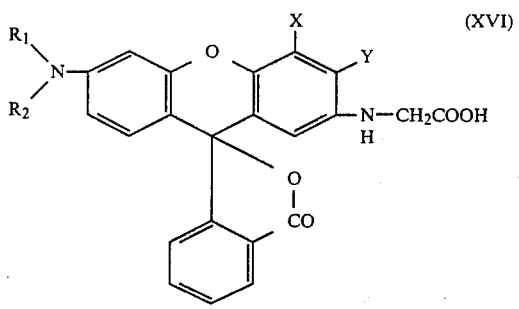

(XVI)

wherein $R_1$, $R_2$, X and Y are the same as described above with use of the compounds represented by the general formula:

$$Q_2-CH_2CH=CH_2 \qquad (XVII)$$

wherein $Q_2$ is halogen atom.

In the above (a) or (b) method, it is preferred to use a catalyst and/or an organic solvent. Among the useful catalyst materials, there are included basic materials such as sodium hydroxide, potassium hydroxide, sodium hydrogencarbonate, potassium hydrogencarbonate, sodium carbonate, potassium carbonate, sodium acetate and potassium acetate; and amines such as trimethylamine and pyridine. Among the useful organic solvents, there are included aromatic hydrocarbon type solvents such as benzene and xylene; halogenated aliphatic hydrocarbon type solvents such as chloroform, bromoform and methylchloroform; halogenated aromatic hydrocarbon type solvents such as chlorobenzene, bromobenzene and dichlorobenzene; alcohol type solvents such as methyl alcohol, ethyl alcohol and propyl alcohol; ether type solvents such as diethyl ether, dimethyl ether of dimethylene glycol and dimethyl ether of diethylene glycol; sulfoxide type solvents such as dimethyl sulfoxide and diethyl sulfoxide; and amide type solvents such as N,N-diethylformamide and dimethylacetamide.

The fluoran derivatives thus obtained according to the invention are substantially colorless chromogenic compounds which can develop a deep color of substantially black upon contact with acceptors. The above mentioned fluoran derivatives may be used either solely or in combination.

The acceptors used are selected according to the kinds of record materials. The materials which are preferably used as acceptors for pressure sensitive record materials, heat sensitive record materials, electrothermal record material, ultrasonic record materials, electrostatic record materials, typewriter's ribbons, ballpoint pen ink and crayon are those which function as Brønsted or Lewis acid. Among them there are included: inorganic acceptors such as acid clay, activated clay, attapulgite, bentonite, colloidal silica, aluminum silicate, magnesium silicate, zinc silicate, tin silicate, calcined kaolin and talc; organic acceptors such as aliphatic carboxylic acids, e.g., oxalic acid, maleic acid, tartaric acid, citric acid, succinic acid and stearic acid, aromatic carboxylic acids, e.g., benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid, 3-phenyl-5-($\alpha,\alpha$-dimethylbenzyl)salicylic acid, 3,5-di-($\alpha$-methylbenzyl)-salicylic acid and 2-hydroxy-1-benzyl-3-naphthoic acid, phenolic compounds, e.g., 4,4'-isopropylidenediphenol, 4,4'-isopropylidenebis(2-chlorophenol), 4,4'-isopropylidenebis(2,6-dibromophenol), 4,4'-isopropylidenebis(2,6-dichlorophenol), 4,4'-isopropylidenebis(2-methylphenol), 4,4'-isopropylidenebis(2,6-dimethylphenol), 4,4'-isopropylidenebis(2-tert-butylphenol), 4,4'-sec-butylidenebisphenol, 4,4'-cyclohexylidenebisphenol, 4,4'-cyclohexylidenebis(2-methylphenol), 4-tert-butylphenol, 4-phenylphenol, 4-hydroxydiphenoxide, $\alpha$-naphthol, $\beta$-naphthol, methyl-4-hydroxybenzoate, benzyl-4-hydroxybenzoate, 2,2'-thiobis-4,6-dichlorophenol), 4-tert-octylcatechol, 2,2'-methylenebis(4-chlorophenol), 2,2'-methylenebis(4-methyl-6-tert-butylphenol) and 2,2'-dihydroxydiphenyl, phenol resins, e.g., p-phenylphenolformaldehyde resin and p-butylphenolacetylene resin; salts of the above organic acceptors with polyvalent metals such as zinc, magnesium, aluminium, calcium, titanium, manganese, tin and nickel; and inorganic acid such as hydrogen halide, e.g., hydrogen chloride, hydrogen bromide and hydrogen iodide, boric acid, solicic acid, phosphoric acid, sulfuric acid, nitric acid, perchloric acid and halides of aluminium, zinc, nickel, tin, titanium, boron and the like.

In case of electron beam record materials or photosensitive record materials, compounds which can produce by electron beam or light radiation, hydrogen halogenides, such as hydrogen chloride, hydrogen bromide and hydrogen iodide, carboxylic acids, sulfonic acids or phenols are preferably used as acceptor materials. Among those compounds, there are included organic halogen compounds, such as carbon tetrabromide, $\alpha,\alpha,\alpha$-tribromoacetophenone, hexachloroethane, iodoform, 2-tribromomethylpyridine and trichloromethyl sulfonylbenzene, o-quinonediazido compounds, phenol esters of carboxylic acid or sulfonic acid which can cause Fries rearrangement, and the like.

Some embodiments of the utilization of the fluoran derivatives according to the invention for various kinds of record materials are described hereinbelow:

The fluoran derivatives can be utilized for various kinds of pressure sensitive record materials, e.g., those disclosed in U.S. Pat. Nos. 2,505,470, 2,505,471, 2,505,489, 2,548,366, 2,712,507, 2,730,456, 2,730,457, 3,418,250, 3,924,027 and 4,010,038.

A typical method for the production of a pressure sensitive record material utilizing the fluoran derivatives according to the invention is as follows:

At least one of the fluoran derivatives according to the invention is dissolved in a solvent to form a solution which may include synthetic oil such as alkylated naphthalene, alkylated diphenyl, alkylated diphenylmethane and alkylated terphenyl, vegetable oil such as cotton seed oil and castor oil, animal oil and mineral oil or mixtures of the foregoing. The solution may additionally include basic colorless chromogenic material such as triphenylmethane lactones, spiropyrans, fluorans, diphenylmethanes and Leucomethylene Blue. The solution of the fluoran derivative may be dispersed in a binder to form a coating composition. The solution may be enclosed in microcapsules through the utilization of the coacervation technique, the interfacial polymerization technique, the in-situ polymerization technique or any other method for making oil droplet-containing microcapsules and the microcapsules thus prepared are dispersed in a binder to form a coating composition. Any one of the coating compositions thus prepared is applied to a base sheet such as a paper sheet, plastic sheet, resin coated paper sheet, etc. to obtain a pressure sensitive record material. In case where the pressure sensitive copying system consists of a top sheet, a bottom sheet and, if necessary, at least one middle sheet, the pressure sensitive record material according to the invention is used as the top sheet and the middle sheet. The pressure sensitive record material according to the invention also be utilized in the "self contained" system in which both the colorless chromogenic material and the acceptor are dispersed on one surface of the same sheet. The pressure sensitive record material utilizing the fluoran derivative according to the invention can produce clear color images having a good light resistance.

The fluoran derivatives according to the invention are also useful for production of various kinds of heat sensitive record materials, e.g., as disclosed in Japanese Patent Publication Nos. 3,680 of 1969, 27,880 of 1969, 14,039 of 1970, 43,830 of 1973, 69 of 1974, 70 of 1974 and 20,142 of 1977. Most typically, heat sensitive record materials may be produced by coating a coating composition including a binder, fine particles of the fluoran derivative according to the invention and the acceptor on a base sheet such as paper sheet, plastic film, synthetic paper sheet, woven fabric sheet or mold. The amount of the acceptor in the recording layer may be within the range of 1 to 50 parts by weight, preferably within the range of 2 to 10 parts by weight, per one part by weight of the chromogenic material used. The coating composition may include inorganic metal compounds such as oxides, hydroxides and carbonates of polyvalent metals and/or inorganic pigments in an amount of 0.1 to 5 parts by weight, preferably, 0.2 to 2 parts by weight, per one part by weight of the amount of the acceptor. The recording layer may also include dispersing agents, ultraviolet ray absorbing agents, heat fusible materials, antifoaming agent, fluorescent dye, coloring dyes and other adding materials.

The fluoran derivative and the acceptor may be applied to a base sheet either in the form of a single coating composition or in the form of two separate coating compositions which may be applied one by one. Application of the fluoran derivative and acceptor to a base sheet may also be carried out by impregnation or by sizing. The amount of the coating composition including the fluoran derivative and the acceptor may preferably be within the range of 2 to 12 g/cm². Among the useful binder materials there may be included starches, celluloses, proteins, gum arabic, polyvinyl alcohol, salts of styrene-maleic anhydride copolymer, styrene-butadiene copolymer emulsions, salts of vinyl acetate-maleic anhydride copolymer and salts of polyacrylic acid.

The electrothermal record materials may be produced according to any know methods such as those disclosed in Japanese Laid-Open Patent Publication Nos. 11,344 of 1974 and 48,930 of 1975. Usually, the record material of this type may be produced, either by coating on a base sheet such as a paper sheet a coating composition consisting of a dispersion of an electroconductive material, a basic dye material essentially comprising the fluoran derivative according to the invention, an acceptor and a binder, or by coating an electroconductive material on a basic sheet to form an electroconductive layer thereon and further coating on the electroconductive layer another coating composition consisting of a dispersion of the fluoran derivative according to the invention, an acceptor and a binder. In case where each of the fluoran derivative and the acceptor used is not fusible within the temperature range of 70° to 120° C., an appropriate heat fusible material may be added for controlling the heat sensitivity.

The photosensitive record materials in which the fluoran derivatives according to the invention are utilized may be produced in a similar manner to any of those disclosed in Japanese Patent Publication Nos. 24,188 of 1963, 10,550 of 1970, 13,258 of 1970, 204 of 1974, 6,212 of 1974 and 28,449 of 1974 and Japanese Laid-Open Patent Publication Nos. 31,615 of 1972, 32,532 of 1973, 9,227 of 1974, 135,617 of 1974, 80,120 of 1975, 87,317 of 1975 and 126,228 of 1975.

The invention is also applicable to other recording systems, such as, the ultrasonic record material, e.g., as disclosed in French Patent Specification No. 2,120,922, the electron beam recording system, e.g., as disclosed in Belgian Pat. No. 7,959,986, the electrostatic record material, e.g., as disclosed in Japanese Patent Publication No. 3,932 of 1974, the photosensitive printing material, e.g., as disclosed in Japanese Laid-Open Patent Publication No. 12,104 of 1973, the seal stamping material, e.g., as disclosed in Japanese Patent Publication No. 10,766 of 1972, type ribbons as disclosed in Japanese Laid-Open Patent Publication No. 3,713 of 1974, ball-point pen ink as disclosed in Japanese Laid-Open Patent Publication No. 83,924 of 1973 and crayon as disclosed in U.S. Pat. No. 3,769,045, by merely using the fluoran derivatives instead of the conventional basic colorless chromogenic materials.

PREFERRED EMBODIMENTS OF THE INVENTION

The following examples serve to illustrate the invention in more detail although the invention is not limited to the examples. Unless otherwise indicated, parts and % signify parts by weight and % by weight, respectively.

EXAMPLE 1

0.011 moles of 2-(2-hydroxy-4-diethylamino)benzoylbenzoic acid was reacted with 0.010 moles of 3-methyl-4-(α-naphthyl)aminoanisole in 10 ml of concentrated sulfuric acid at room temperature for 24 hours. The obtained material was poured into 100 ml of ice-cold water and then the resultant liquid was neutralized with 20% aqueous solution of sodium hydroxide at room temperature to obtain a solid. The solid was filtered off and washed with cold water. Then the all amount of the solid was added into 80 ml of a solution of acetone/water (3/5). The aqueous system was adjusted to pH 11 and refluxed for 3 hours and then acetone was removed to obtain 3-diethylamino-6-methyl-7-α-naphthylaminofluoran in the form of crystals. The crystals were recrystallized from toluene to obtain colorless crystals having a melting point of 205°–206° C. in 87% yield. The colorless crystals became reddish black upon contact with silica gel.

EXAMPLE 2

0.01 moles of 2-(2-hydroxy-4-dibenzylamino)benzoylbenzoic acid was reacted with 0.01 moles of 3-methyl-4-(α-naphthyl)aminoanisole in 20 ml of concentrated sulfuric acid at room temperature for 24 hours. The obtained material was poured into 150 ml of ice-cold water and then the resultant material was neutralized with 20% aqueous solution of sodium hydroxide to obtain a solid. The solid was filtered off and washed with cold water. Then the all amount of the solid was put in a flask, and 10 ml of toluene and 30 ml of an aqueous solution of sodium hydroxide adjusted to pH 11.5 were added into the flask. The resultant mixture was reacted with stirring at 85° C. for 3 hours and then allowed to stand for 24 hours to obtain 3-dibenzylamino-6-methyl-7-α-naphthylaminofluoran in the form of crystals. The crystals were recrystallized from benzene to obtain colorless crystals having a melting point of 211°–215° C. in 83% yield. The colorless crystals became reddish black upon contact with silica gel.

EXAMPLE 3

0.01 moles of 2-(2-hydroxy-4-N-methyl-N-n-hexylamino)benzoylbenzoic acid was reacted with 0.01 moles of 3-methyl-4-(α-naphthyl)aminophenol in 15 ml of concentrated sulfuric acid at room temperature for 24 hours. The obtained material was poured into 150 ml of ice-cold water and neutralized with 20% aqueous solution of sodium hydroxide at room temperature to obtain a solid. The solid was filtered off, washed and dried. The dried material was recrystallized from ethyl alcohol to obtain 3-N-methyl-N-n-hexylamino-6-methyl-7-α-naphthylaminofluoran in the form of colorless crystals having a melting point of 158°–162° C. in 53% yield. The crystals became reddish black upon contact with silica gel.

EXAMPLES 4 TO 16

Example 1 was repeated to obtain various fluoran derivatives except that benzophenone derivatives shown in Table 1 were used instead of 2-(2-hydroxy-4-diethylamino)benzoylbenzoic acid and α-naphthylamine derivatives shown in Table 1 were used instead of 3-methyl-4-(α-naphthyl)aminoanisole. The yield of the products and the colors formed upon contact with silica gel are shown in Table 1.

TABLE 1

Benzophenone Derivatives $$R_1R_2N-\text{C}_6H_3(OH)-CO-\text{C}_6H_4-COOH$$

α-Naphthylamine Derivatives $$R_5O-\text{C}_6H_2(X)(Y)-NH-\text{naphthyl}-E$$

| Example No. | R₁ | R₂ | X | Y | E | R₅ | Yield (%) | Products Developed Color |
|---|---|---|---|---|---|---|---|---|
| 4 | methyl | methyl | H | ethyl | H | ethyl | 88 | reddish black |
| 5 | n-butyl | n-butyl | H | ethyl | H | ethyl | 89 | reddish black |
| 6 | methyl | n-hexyl | H | chlorine | H | H | 51 | black |
| 7 | ethyl | n-octyl | H | chlorine | H | H | 50 | black |
| 8 | methyl | lauryl | H | chlorine | H | H | 50 | black |
| 9 | methyl | n-amyl | methyl | H | H | H | 56 | greenish black |
| 10 | ethyl | isoamyl | methyl | H | H | H | 51 | greenish black |
| 11 | ethyl | n-butyl | chlorine | H | H | H | 50 | greenish black |
| 12 | ethyl | n-hexyl | chlorine | H | H | H | 53 | greenish black |
| 13 | methyl | β-ethylhexyl | methoxy | H | amino | H | 48 | greenish black |
| 14 | ethyl | isopentyl | methoxy | H | diethylamino | H | 50 | greenish black |
| 15 | ethyl | benzyl | t-butyl | H | anilino | H | 47 | greenish black |
| 16 | isoamyl | n-hexyl | H | methyl | amino | H | 43 | reddish black |

EXAMPLE 17

A heat-sensitive record material was prepared by the following method with the use of 3-diethylamino-6-methyl-7-α-naphthylaminofluoran obtained in Example 1.

(1) Preparation of A liquid:

The following composition was passed through a sand mill.

| | |
|---|---|
| fluoran derivative obtained in Example 1 | 5 parts |
| stearic acid amide | 1 parts |
| 2% aqueous solution of hydroxyethylcellulose | 25 parts |

Pulverization was continued until an average particle size of 2 microns.

(2) Preparation of B liquid:

The following composition was passed through a sand mill.

| | |
|---|---|
| 4,4′-isopropylidenediphenol | 50 parts |
| stearic acid amide | 10 parts |
| 2% aqueous solution of hydroxyethylcellulose | 250 parts |

Pulverization was continued until an average particle size of 2 microns.

(3) Making a heat-sensitive record material:

The following composition was mixed to prepare a coating composition.

| | |
|---|---|
| A liquid | 62 parts |
| B liquid | 31 parts |
| ultrafinely divided particles of silicic anhydride ("Syloid 244" manufactured by Fuji-Davidson Chemical) | 25 parts |
| 20% aqueous solution of a salt of styrene-maleic anhydride copolymer | 175 parts |
| zinc stearate | 5 parts |
| water | 100 parts |

The coating composition was coated on a base sheet of 50 g/m² in the weight of an amount of 6 g/m² on dry basis to obtain a heat-sensitive record material.

The heat-sensitive record material was pressed with a pressure of 4 kg/cm² for 5 seconds on a plate heated at 125° C. to develop deep black images. The color images were superior in light resistance. The color change and discoloration when exposed to sunlight were not substantially appreciated.

EXAMPLE 18

5 parts of fluoran derivative obtained in Example 1 was dissolved in 100 parts of isopropylated naphthalene. The resultant solution was dispersed in 350 parts of warm water (50° C.) containing 25 parts of pigskin-gelatin having an isoelectric point of 8 and 25 parts of gum arabic dissolved in it to obtain an emulsion. 1000 parts of warm water was added to the emulsion. The mixture was adjusted to pH 4 with acetic acid and cooled at 10° C. 10 parts of 25% aqueous solution of glutaraldehyde was added to it to solidify capsules. The capsule-containing coating composition was coated on one surface of a base sheet of 45 g/m² in the weight of 5 g/m² on dry basis and an acceptor coating composition comprising 20 parts of zinc 3,5-bis(α-methylbenzyl)salicylate, 80 parts of kaolin and 30 parts of styrene-butadiene copolymer emulsion (solid content: 50%) dispersed in 200 parts of water was coated on another surface of the base sheet in the weight of 5 g/m² on dry basis to obtain a pressure-sensitive record material (middle sheet).

Several of the pressure-sensitive record material were piled in the manner as the capsule coated layer was closed to the acceptor coated layer, pressed with driving a pen to obtain black color images on the acceptor coated surface. The color images were stable to water and alcohol and when exposed to sunlight the color change and discoloration were not appreciated.

EXAMPLE 19

200 parts of cuprous iodide and 5 parts of 10% aqueous solution of sodium sulfite were added to 200 parts of 1% aqueous solution of polyvinyl alcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m² in the weight of 7 g/m² on dry basis. Further, there was coated on the coating layer in the weight of 5 g/m² on dry basis a heat-sensitive coating composition prepared by the same manner as in Example 17 to obtain an electrothermal record material.

Images were recorded on the record material with the use of a cylindrical scanning recording machine at a scanning speed of 630 mm/sec with a needle pressure of 10 g. The record images were deep black. The color images were superior in light resistance. The color change and discoloration when exposed to sunlight were not substantially appreciated.

EXAMPLE 20

6 g of 3-N-methyl-N-n-hexylamino-6-methyl-7-α-naphthylaminofluoran obtained in Example 3 was dissolved in 40 ml of chloroform. 40 ml of 10% benzene solution of polystyrene and 5 g of carbon tetrabromide were added to the solution and the mixture was thoroughly stirred to prepare a coating composition. The coating composition was coated on polyethylene laminated paper having polyethylene at the both surfaces in the weight of 5 g/m² on dry basis in a dark place. The coated paper was irradiated with a light of eight ultraviolet lamps of 20 W from a distance of 5 cm for 10 minutes to develop black color images. The color images were then fixed by rinsing with a solution of acetone/n-hexane (1/5). The resultant images were stable when exposed to sunlight.

EXAMPLE 21

0.011 moles of 2-(2-hydroxy-4-diethylamino)benzoyl-benzoic acid was reacted with 0.010 moles of 3-methyl-4-methoxy-4'-acetyldiphenylamine in 15 ml of concentrated sulfuric acid at room temperature for 24 hours. The obtained material was poured into 100 ml of ice-cold water and the aqueous system was adjusted to pH 11 by adding 20% aqueous solution of sodium hydroxide at room temperature. Then 50 ml of toluene was added to the aqueous system and heated at 85° C. for 3 hours. The toluene layer was taken out of the mixture and then toluene was removed by vacuum distillation to obtain a solid. The solid was recrystallized from methyl alcohol to obtain 3-diethylamino-5-methyl-7-(p-acetylanilino)fluoran, having a melting point of 182°–183° C. in 85% yield. Thus obtained fluoran derivative became black upon contact with silica gel.

EXAMPLE 22

0.01 moles of 2-(2-hydroxy-4-diethylamino)benzoyl-benzoic acid was reacted with 0.01 moles of 2-methyl-4-ethoxy-3'-acetyldiphenylamine in 10 ml of concentrated sulfuric acid at room temperature for 24 hours. The obtained material was poured into 100 ml of ice-cold water and the aqueous system was adjusted to pH 11 by adding 20% aqueous solution of sodium hydroxide at room temperature. 30 ml of acetone was added to the aqueous system and the mixture was refluxed for 3 hours. Then acetone was removed to obtain a solid in the form of crystals. The solid was filtered off, washed with water and then recrystallized from isopropyl alcohol to obtain 3-diethylamino-6-methyl-7-(m-acetylanilino)fluoran having a melting point 216°–217° C. in 81% yield. The fluoran derivative became black upon contact with silica gel.

EXAMPLE 23

0.02 moles of 2-(2-hydroxy-4-N-ethyl-N-benzylamino)benzoylbenzoic acid was reacted with 0.01 moles of 3-methoxy-4-hydroxy-2'-benzoyl-diphenylamine in 30 ml of concentrated sulfuric acid at room temperature for 7 hours. The obtained material was poured into 100 ml of ice-cold water and the aqueous system was adjusted to pH 9 by adding 20% aqueous solution of sodium hydroxide at room temperature to obtain a precipitate. The precipitate was filtered off, washed with water, dried and then recrystallized from benzene to obtain 3-diethylamino-5-methoxy-7-(o-benzoylanilino)fluoran having a melting point of 201°–202° C. in 57% yield. The fluoran derivative became reddish black upon contact with silica gel.

EXAMPLES 24 TO 33

Example 21 was repeated to obtain various fluoran derivatives except that benzophenone derivatives shown in Table 2 were used instead of 2-(2-hydroxy-4-diethylamino)benzoylbenzoic acid and that diphenylamine derivatives shown in Table 2 were used instead of 3-methyl-4-methoxy-4'-acetyldiphenylamine. The yield of the products and the colors formed upon contact with silica gel are shown in Table 2.

TABLE 2

| | Benzophenone Derivatives | | | Diphenylamine Derivatives | | | | Products | |
|---|---|---|---|---|---|---|---|---|---|
| Example No. | $R_1$ | $R_2$ | X | Y | —CO—A | $R_5$ | Yield (%) | Developed Color |
| 24 | methyl | methyl | methyl | H | o-acetyl | methyl | 80 | reddish black |
| 25 | n-butyl | n-butyl | methyl | H | m-acetyl | ethyl | 85 | greenish black |
| 26 | methyl | n-butyl | ethyl | H | p-acethyl | ethyl | 82 | black |
| 27 | methyl | n-octyl | H | ethyl | p-butanoyl | methyl | 86 | reddish black |
| 28 | ethyl | n-butyl | H | methyl | o-acetyl | methyl | 89 | reddish black |
| 29 | ethyl | n-hexyl | H | chlorine | p-acetyl | methyl | 89 | reddish black |
| 30 | ethyl | β-ethylhexyl | methyl | H | p-(o-chlorobenzoyl) | H | 53 | black |
| 31 | ethyl | isopentyl | methyl | H | p-(p-methylbenzoyl) | H | 60 | reddish black |
| 32 | n-butyl | n-octyl | methoxy | H | o-naphthoyl | H | 51 | reddish black |

TABLE 2-continued

Benzophenone Derivatives / Diphenylamine Derivatives

| Example No. | R₁ | R₂ | X | Y | —CO—A | R₅ | Yield (%) | Products Developed Color |
|---|---|---|---|---|---|---|---|---|
| 33 | n-butyl | lauryl | t-butyl | H | o-benzoyl | H | 55 | reddish black |

EXAMPLE 34

A heat-sensitive record material was prepared in the same manner as in Example 17 except that 3-diethylamino-5-methyl-7-(p-acetylanilino)fluoran obtained in Example 21 was used instead of 3-diethylamino-6-methyl-7-α-naphthylaminofluoran.

The obtained record material which had a good white paper appearance without fogging, was pressed with a pressure of 4 kg/cm² for 5 seconds on a plate heated at 125° C. to develop deep black images. The color images were superior in light resistance. The color change and discoloration when exposed to sunlight were not substantially appreciated.

Images were recorded on the record material with the use of a cylindrical scanning recording machine at a scanning speed of 0.7 m/sec with $CO_2$ gas laser (output: 1 W, beam diameter: 150 microns). Resultantly, deep black images were obtained.

EXAMPLE 35

A pressure-sensitive record material was prepared in the same manner as in Example 18 except that fluoran derivative obtained in Example 21 was used instead of fluoran derivative obtained in Example 1.

Several of the pressure-sensitive record material were piled in the manner as the capsule coated layer was closed to the acceptor coated layer, pressed with driving a pen to obtain black color images on the acceptor coated surface. The color images were obtained with a rapid color development and in a deep color immediately after press, and the color change and discoloration were not appreciated when exposed to sunlight.

EXAMPLE 36

200 parts of cuprous iodide and 5 parts of 10% aqueous solution of sodium sulfite were added to 200 parts of b 1% aqueous solution of polyvinyl alcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m² in the weight of 7 g/m² on dry basis. Further, there was coated on the coating layer in the weight of 5 g/m² on dry basis a heat-sensitive coating composition prepared by the same manner as in Example 34 except that 3-diethylamino-6-methyl-7-(m-acetylanilino)fluoran obtained in Example 22 was used instead of 3-diethylamino-5-methyl-7-(p-acetylanilino)-fluoran to obtain an electrothermal record material.

Images were recorded on the record material with the use of a cylindrical scanning recording machine at a scanning speed of 630 mm/sec with a needle pressure of 10 g. The recorded images were deep black. The color images were superior in light resistance. The color change and discoloration when exposed to sunlight were not substantially appreciated.

EXAMPLE 37

6 g of 3-diethylamino-6-methyl-7-(m-acetylanilino)-fluoran obtained in Example 22 was dissolved in 40 ml of chloroform. 40 ml of 10% benzene solution of polystyrene and 5 g of carbon tetrabromide were added to the solution and the mixture was thoroughly stirred to prepare a coating composition. The coating composition was coated on polyethylene laminated paper having polyethylene at the both surfaces in the weight of 5 g/m² on dry basis in a dark place. The coated paper was irradiated with a light of eight ultraviolet lamps of 20 W from a distance of 5 cm for 10 minutes to develop black color images. The color images were then fixed by rinsing with a solution of acetone/n-hexane(1/5). The resultant images were stable when exposed to sunlight.

EXAMPLE 38

0.011 moles of 2-(2-hydroxy-4-diethylamino)benzoylbenzoic acid was reacted with 0.010 moles of p-(N-carboallyloxymethyl)aminophenol in 10 ml of concentrated sulfuric acid at room temperature for 24 hours. The obtained material was poured into 100 ml of ice-cold water and the aqueous system was adjusted to pH 9 by adding 20% aqueous solution of sodium hydroxide at room temperature to obtain a precipitate. The precipitate was filtered off, washed with water, dried and recrystallized from methyl alcohol to obtain 3-diethylamino-7-(N-carboallyloxymethyl)aminofluoran having a melting point of 159°–160° C. in 47% yield.

Thus obtained fluoran derivative became black upon contact with silica gel.

EXAMPLE 39

0.013 moles of 2-(2-hydroxy-4-diethylamino)benzoylbenzoic acid was reacted with 0.010 moles of methyl ether of 3-methyl-4-aminophenol in 10 ml of concentrated sulfuric acid at room temperature for 24 hours. The obtained material was poured into 100 ml of ice-cold water and the aqueous system was adjusted to pH 11 by adding 20% aqueous solution of sodium hydroxide at room temperature. Then 20 ml of toluene was added to the aqueous system. The mixture was heated at 85° C. for 3 hours and then cooled on standing to produce 3-diethylamino-6-methyl-7-aminofluoran in the crystal form in the toluene layer.

0.01 moles of thus obtained fluoran derivative was added to 50 ml of n-propylalcohol. Further, to the mixture 0.01 moles of sodium hydrogencarbonate, 0.01 moles of potassium iodide and 0.01 moles of carboallyloxymethyl chloride were added and the mixture was refluxed for 2 hours. After cooling on standing, the insoluble materials were filtered off and n-propylalcohol was removed by vacuum distillation. Water adjusted to pH 8 was added to the residue to produce a slurry. The slurry was extracted with benzene.

The benzene layer was dehydrated by adding anhydrous sodium sulfate and then concentrated. The concentrate was recrystallized with an equal portion of cyclohexane to obtain 3-diethylamino-6-methyl-7-(N-carboallyloxymethyl)aminofluoran having a melting point of 149°–150° C. in 57% yield. Thus obtained fluoran derivative became reddish black upon contact with silica gel.

EXAMPLE 40

0.01 moles of 2-(2-hydroxy-4-N-methyl-N-benzylamino)benzoylbenzoic acid was reacted with 0.01 moles of N-p-hydroxyphenylglycine in 10 ml of concentrated sulfuric acid at room temperature for 40 hours. The obtained material was poured into 100 ml of ice-cold water and the mixture was neutralized with 20% aqueous solution of sodium hydroxide to produce a precipitate. The precipitate was filtered off and dissolved in 50 ml of an aqueous solution of sodium hydroxide at pH 10. To the aqueous system 20 ml of benzene solution containing 0.02 moles of allyl chloride dissolved in it was added. The mixture was refluxed for 6 hours with vigorous stirring to react. The benzene layer was separated and benzene was removed by vacuum distillation. The residue was recrystallized from ethyl alcohol to obtain 3-N-methyl-N-benzylamino-7-(N-carboallyloxymethyl)aminofluoran in the form of colorless crystals in 31% yield. The fluoran derivative had a melting point of 151°–153° C. and became black upon contact with silica gel.

EXAMPLE 41 TO 53

Example 38 was repeated to obtain various fluoran derivatives except that benzophenone derivatives shown in Table 3 were used instead of 2-(2-hydroxy-4-diethylamino)benzoylbenzoic acid and that p-aminophenol derivatives shown in Table 3 were used instead of p-(N-carboallyloxymethyl)aminophenol. The yield of the products and the colors formed upon contact with silica gel are shown in Table 3.

EXAMPLE 54

A heat-sensitive record material was prepared in the same manner as in Example 17 except that 3-diethylamino-7-(N-carboallyloxymethyl)aminofluoran obtained in Example 38 was used instead of 3-diethylamino-6-methyl-7-α-naphthylaminofluoran.

The obtained record material which had a good white paper like appearance without fogging, was pressed with a pressure of 4 kg/cm$^2$ for 5 seconds on a plate heated at 125° C. to develop deep black images. The color images were superior in light resistance. The color change and discoloration when exposed to sunlight were not substantially appreciated.

Images were recorded on the record material with the use of a cylindrical scanning recording machine at a scanning speed of 0.7 m/sec with $CO_2$ gas laser (output: 1 W, beam diameter: 150 microns). Resultantly, deep black images were obtained.

EXAMPLE 55

A pressure-sensitive record material was prepared in the same manner as in Example 18 except that 3-diethylamino-6-methyl-7-(N-carboallyloxymethyl)aminofluoran obtained in Example 39 was used instead of fluoran derivative obtained in Example 1.

Several of the pressure-sensitive record material were piled in the manner as the capsule coated layer was closed to the acceptor coated layer, pressed with driving a pen to obtain reddish black color images on the acceptor coated surface. The color images were obtained with a rapid color development and in a deep color immediately after press, and the color change and discoloration were not appreciated when exposed to sunlight.

EXAMPLE 56

200 parts of cuprous iodide and 5 parts of 10% aqueous solution of sodium sulfite were added to 200 parts of 1% aqueous solution of polyvinyl alcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m$^2$ in the weight of 7 g/m$^2$ on dry basis. Further,

TABLE 3

| | Benzophenone Derivatives | | p-Aminophenyl Derivatives | | | | |
|---|---|---|---|---|---|---|---|
| Example No. | $R_1$ | $R_2$ | X | Y | $R_5$ | Yield (%) | Products Developed Color |
| 41 | methyl | ethyl | methyl | H | H | 49 | black |
| 42 | methyl | n-amyl | H | ethyl | H | 45 | reddish black |
| 43 | methyl | n-butyl | H | chlorine | H | 48 | black |
| 44 | methyl | n-hexyl | chlorine | H | H | 48 | black |
| 45 | ethyl | n-hexyl | methyl | H | H | 49 | black |
| 46 | ethyl | isoamyl | methyl | H | H | 45 | black |
| 47 | isoamyl | n-hexyl | H | methyl | H | 43 | reddish black |
| 48 | n-butyl | n-butyl | H | chlorine | H | 47 | black |
| 49 | ethyl | n-butyl | H | H | H | 51 | black |
| 50 | ethyl | isopentyl | H | H | H | 46 | black |
| 51 | ethyl | β-ethylhexyl | methoxy | H | H | 45 | reddish black |
| 52 | ethyl | n-octyl | methoxy | H | H | 47 | reddish black |
| 53 | ethyl | lauryl | t-butyl | H | H | 43 | black | there was coated on the coating layer in the weight of 5 g/m² on dry basis a heat-sensitive coating composition prepared by the same manner as in Example 54 except that 3-diethylamino-6-methyl-7-(N-carboallyloxymethyl)aminofluoran obtained in Example 39 was used instead of 3-diethylamino-7-(N-carboallyloxymethyl)aminofluoran to obtain an electrothermal record material.

Images were recorded on the record material with the use of a cylindrical scanning recording machine at a scanning speed of 630 mm/sec with a needle pressure of 10 g. The recorded images were deep black. The color images were superior in light resistance. The color change and discoloration when exposed to sunlight were not substantially appreciated.

EXAMPLE 57

6 g of 3-N-methyl-N-benzylamino-7-(N-carboallyloxymethyl)aminofluoran obtained in Example 40 was dissolved in 40 ml of chloroform. 40 ml of 10% benzene solution of polystyrene and 5 g of carbon tetrabromide were added to the solution and the mixture was thoroughly stirred to prepare a coating composition. The coating composition was coated on polyethylene laminated paper having polyethylene at the both surfaces in the weight of 5 g/m² on dry basis in a dark place. The coated paper was irradiated with a light of eight ultraviolet lamps of 20 W from a distance of 5 cm for 10 minutes to develop black color images. The color images were then fixed by rinsing with a solution of acetone/n-hexane(1/5). The resultant images were stable when exposed to sunlight.

EXAMPLE 58

0.011 moles of 2-(2-hydroxy-4-diethylamino)benzoylbenzoic acid was reacted with 0.010 moles of 4-methoxy-4'-benzoyldiphenylamine in 15 ml of concentrated sulfuric acid at room temperature for 24 hours. The obtained material was poured into 100 ml of ice-cold water. The aqueous system was adjusted to pH 11 by adding 20% aqueous solution of sodium hydroxide at room temperature and then mixed with 50 ml of toluene. The mixture was heated at 85° C. for 3 hours. The toluene layer was separated, and then toluene was removed by vacuum distillation. The residue was recrystallized from methyl alcohol to obtain 3-diethylamino-7-(p-benzoylanilino)fluoran having a melting point of 216°–218° C. in 87% yield. The fluoran derivative became black upon contact with silica gel.

EXAMPLE 59

0.01 moles of 2-(2-hydroxy-4-diethylamino)benzoylbenzoic acid was reacted with 0.01 moles of 4-ethoxy-3'-benzoyldiphenylamine in 10 ml of concentrated sulfuric acid at room temperature for 24 hours. The obtained material was poured into 100 ml of ice-cold water. The aqueous system was adjusted to pH 11 by adding 20% aqueous solution of sodium hydroxide at room temperature and was mixed with 30 ml of acetone. The mixture was refluxed for 3 hours and then acetone was removed to precipitate a solid in the form of crystals. The solid was filtered off, washed with water and recrystallized from isopropyl alcohol to obtain 3-diethylamino-7-(m-benzoylanilino)fluoran having a melting point of 222°–226° C. in 85% yield. The fluoran derivative became greenish black upon contact with silica gel.

EXAMPLE 60

0.02 moles of 2-(2-hydroxy-4-N-ethyl-N-benzylamino)benzoylbenzoic acid was reacted with 0.01 moles of 4-hydroxy-2'-benzoyldiphenylamine in 30 ml of concentrated sulfuric acid at room temperature for 7 hours. The obtained material was poured into 100 ml of ice-cold water and the aqueous system was adjusted to pH 9 by adding 20% aqueous solution of sodium hydroxide at room temperature to produce a precipitate. The precipitate was filtered off, washed with water and recrystallized from benzene to obtain 3-N-ethyl-N-benzylamino-7-(o-benzoylanilino)fluoran having a melting point of 183°–189° C. in 63% yield. The fluoran derivative became black upon contact with silica gel.

EXAMPLES 61 TO 68

Example 58 was repeated to obtain various fluoran derivatives except that benzophenone derivatives shown in Table 4 were used instead of 2-(2-hydroxy-4-diethylamino)benzoylbenzoic acid and that diphenylamine derivatives shown in Table 4 were used instead of 4-methoxy-4'-benzoyldiphenylamine. The yield of the products and the colors formed upon contact with silica gel are shown in Table 4.

TABLE 4

| | Benzophenone Derivatives | | Diphenylamine Derivatives | | | |
|---|---|---|---|---|---|---|
| Example No. | $R_1$ | $R_2$ | —CO—A | $R_5$ | Yield (%) | Products Developed Color |
| 61 | methyl | methyl | p-benzoyl | methyl | 85 | black |
| 62 | methyl | n-butyl | p-benzoyl | methyl | 88 | black |
| 63 | methyl | n-hexyl | p-benzoyl | methyl | 83 | black |
| 64 | ethyl | n-butyl | p-benzoyl | methyl | 86 | black |
| 65 | ethyl | n-amyl | p-benzoyl | methyl | 85 | black |
| 66 | ethyl | n-hexyl | p-benzoyl | methyl | 81 | black |
| 67 | n-butyl | n-butyl | p-benzoyl | methyl | 84 | black |
| 68 | isoamyl | isoamyl | p-(p-methylbenzoyl) | methyl | 75 | black |

EXAMPLES 69 TO 71

Example 60 was repeated to obtain various fluoran derivatives except that benzophenone derivatives shown in Table 5 were used instead of 2-(2-hydroxy-4-N-ethyl-N-benzylamino)benzoylbenzoic acid and that diphenylamine derivatives shown in Table 5 were used instead of 4-hydroxy-2'-benzoyldiphenylamine. The yield of the products and the colors formed upon contact with silica gel are shown in Table 5.

Images were recorded on the record material with the use of a cylindrical scanning recording machine at a scanning speed of 630 mm/sec with a needle pressure of 10 g. The recorded images were dark greenish black.

TABLE 5

| | Benzophenone Derivatives | | Diphenylamine Derivatives | | | |
|---|---|---|---|---|---|---|
| | | | | | | Products |
| Example No. | $R_1$ | $R_2$ | —CO—A | $R_5$ | Yield (%) | Developed Color |
| 69 | methyl | ethyl | o-benzoyl | H | 61 | black |
| 70 | ethyl | ethyl | o-benzoyl | H | 63 | black |
| 71 | ethyl | isoamyl | o-benzoyl | H | 60 | black |

EXAMPLE 72

A heat-sensitive record material was prepared in the same manner as in Example 17 except that 3-diethylamino-7-(p-benzoylanilino)fluoran obtained in Example 58 was used instead of 3-diethylamino-6-methyl-7-α-naphthylaminofluoran.

The obtained record material which had a good white paper like appearance without fogging, was pressed with a pressure of 4 kg/cm² for 5 seconds on a plate heated at 125° C. to develop deep black images. The color images were superior in light resistance. The color change and discoloration when exposed to sunlight were not substantially appreciated.

Images were recorded on the record material with the use of a cylindrical scanning recording machine at a scanning speed of 0.7 m/sec with $CO_2$ gas laser (output: 1 W, beam diameter: 150 microns). Resultantly, deep black images were obtained.

EXAMPLE 73

A pressure-sensitive record material was prepared in the same manner as in Example 18 except that fluoran derivative obtained in Example 58 was used instead of fluoran derivative obtained in Example 1.

Several of the pressure-sensitive record material were piled in the manner as the capsule coated layer was closed to the acceptor coated layer, pressed with driving a pen to obtain black color images on the acceptor coated surface. The color images were obtained with a rapid color development and in a deep color immediately after press, and the color change and discoloration were not appreciated when exposed to sunlight.

EXAMPLE 74

200 parts of cuprous iodide and 5 parts of 10% aqueous solution of sodium sulfite were added to 200 parts of 1% aqueous solution of polyvinyl alcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m² in the weight of 7 g/m² on dry basis. Further, there was coated on the coating layer in the weight of 5 g/m² on dry basis a heat-sensitive coating composition prepared by the same manner as in Example 72 except that 3-diethylamino-7-(m-benzoylanilino)fluoran obtained in Example 59 was used instead of 3-diethylamino-7-(p-benzoylanilino)fluoran to obtain an electrothermal record material.

The color images were superior in light resistance. The color change and discoloration when exposed to sunlight were not substantially appreciated.

EXAMPLE 75

6 g of 3-N-ethyl-N-benzylamino-7-(o-benzoylanilino)fluoran obtained in Example 60 was dissolved in 40 ml of chloroform. 40 ml of 10% benzene solution of polystyrene and 5 g of carbon tetrabromide were added to the solution and the mixture was thoroughly stirred to prepare a coating composition. The coating composition was coated on polyethylene laminated paper having polyethylene at the both surfaces in the weight of 5 g/m² on dry basis in a dark place. The coated paper was irradiated with a light of eight ultraviolet lamps of 20 W from a distance of 5 cm for 10 minutes to develop black color images. The color images were then fixed by rinsing with a solution of acetone/n-hexane(1/5). The resultant images were stable when exposed to sunlight.

EXAMPLE 76

0.011 moles of 2-(2-hydroxy-4-diethylamino)benzoylbenzoic acid was reacted with 0.010 moles of 4-(o-biphenyl)aminophenol in 10 ml of concentrated sulfuric acid at room temperature for 24 hours. The obtained material was poured into 100 ml of ice-cold water and the aqueous system was adjusted to pH 9 by adding 20% aqueous solution of sodium hydroxide at room temperature to produce a precipitate. The precipitate was filtered off, washed with water, dried and then recrystallized from methyl alcohol to obtain 3-diethylamino-7-(o-biphenyl)aminofluoran having a melting point of 181°–186° C. in 61% yield. The fluoran derivative became greenish black upon contact with silica gel.

EXAMPLE 77

0.011 moles of 2-(2-hydroxy-4-diethylamino)benzoylbenzoic acid was reacted with 0.010 moles of 3-methyl-4-(p-biphenyl)aminophenol methyl ether in 15 ml of concentrated sulfuric acid at room temperature for 24 hours. The obtained material was poured into 100 ml of ice-cold water and the aqueous system was adjusted to pH 11 by adding 20% aqueous solution of sodium hydroxide at room temperature. 50 ml of toluene was added to the aqueous system and the mixture was heated at 85° C. for 3 hours. The toluene layer was separated and the toluene was removed by vacuum distillation. The residue was recrystallized from methyl alcohol to obtain 3-diethylamino-6-methyl-7-(p-biphenyl)aminofluoran having a melting point of 189°–193° C. in 85% yield. The fluoran derivative became black upon contact with silica gel.

EXAMPLES 78 TO 85

Example 76 was repeated to obtain various fluoran derivatives except that benzophenone derivatives shown in Table 6 were used instead of 2-(2-hydroxy-4-diethylamino)benzoylbenzoic acid and that 4-(o-biphenyl)aminophenol derivatives shown in Table 6 were used instead of 4-(o-biphenyl)aminophenol. The yield of the products and the colors formed upon contact with silica gel are shown in Table 6.

TABLE 6

| | Benzophenone Derivatives | | 4-(o-Biphenyl)aminophenol Derivatives | | | Products | |
|---|---|---|---|---|---|---|---|
| Example No. | $R_1$ | $R_2$ | X | Y | $R_5$ | Yield (%) | Developed Color |
| 78 | methyl | ethyl | H | methyl | H | 63 | black |
| 79 | methyl | n-amyl | H | chlorine | H | 59 | black |
| 80 | methyl | n-butyl | methoxy | H | H | 60 | greenish black |
| 81 | methyl | n-hexyl | methyl | H | H | 55 | greenish black |
| 82 | isoamyl | n-hexyl | t-butyl | H | H | 47 | greenish black |
| 83 | ethyl | n-octyl | chlorine | H | H | 58 | black |
| 84 | ethyl | lauryl | H | H | H | 53 | greenish black |
| 85 | benzyl | benzyl | H | H | H | 60 | greenish black |

EXAMPLES 86 TO 91

Example 77 was repeated to obtain various fluoran derivatives except that benzophenone derivatives shown in Table 7 were used instead of 2-(2-hydroxy-4-diethylamino)benzoylbenzoic acid and that 4-(p-biphenyl)aminophenol derivatives shown in Table 7 were used instead of 3-methyl-4-(p-biphenyl)aminophenol methyl ether. The yield of the products and the colors formed upon contact with silica gel are shown in Table 7.

TABLE 7

| | Benzophenone Derivatives | | 4-(p-Biphenyl)aminophenol Derivatives | | | Products | |
|---|---|---|---|---|---|---|---|
| Example No. | $R_1$ | $R_2$ | X | Y | $R_5$ | Yield (%) | Developed Color |
| 86 | ethyl | n-butyl | H | methyl | ethyl | 87 | black |
| 87 | ethyl | benzyl | H | ethyl | ethyl | 83 | black |
| 88 | methyl | methyl | H | chlorine | methyl | 89 | black |
| 89 | methyl | n-hexyl | methyl | H | ethyl | 80 | greenish black |
| 90 | ethyl | n-hexyl | chlorine | H | methyl | 88 | greenish black |
| 91 | ethyl | isoamyl | H | methyl | methyl | 85 | black |

EXAMPLE 92

A heat-sensitive record material was prepared in the same manner as in Example 17 except that 3-diethylamino-7-(o-biphenyl)aminofluoran obtained in Example 76 was used instead of 3-diethylamino-6-methyl-7-α-naphthylaminofluoran.

The obtained record material which had a good white paper like appearance without fogging, was pressed with a pressure of 4 kg/cm² for 5 seconds on a plate heated at 125° C. to develop dark greenish black images. The color images were superior in light resistance. The color change and discoloration when exposed to sunlight were not substantially appreciated.

Images were recorded on the record material with the use of a cylindrical scanning recording machine at a scanning speed of 0.7 m/sec with $CO_2$ gas laser (output: 1 W, beam diameter: 150 microns). Resultantly, dark greenish black images were obtained.

EXAMPLE 93

A pressure-sensitive record material was prepared in the same manner as in Example 18 except that 3-diethylamino-6-methyl-7-(p-biphenyl)aminofluoran obtained in Example 77 was used instead of fluoran derivative obtained in Example 1.

Several of the pressure-sensitive record material were piled in the manner as the capsule coated layer was closed to the acceptor coated layer, pressed with driving a pen to obtain black color images on the acceptor coated surface. The color images were obtained with a rapid color development and in a deep color immediately after press, and the color change and discoloration were not appreciated when exposed to sunlight.

EXAMPLE 94

200 parts of cuprous iodide and 5 parts of 10% aqueous solution of sodium sulfite were added to 200 parts of 1% aqueous solution of polyvinyl alcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m² in the weight of 7 g/m² on dry basis. Further, there was coated on the coating layer in the weight of 5 g/m² on dry basis a heat-sensitive coating composition prepared by the same manner as in Example 92 except that 3-diethylamino-6-methyl-7-(p-biphenyl)aminofluoran obtained in Example 77 was used instead of 3-diethylamino-7-(o-biphenyl)aminofluoran to obtain an electrothermal record material.

Images were recorded on the record material with the use of a cylindrical scanning recording machine at a scanning speed of 630 mm/sec with a needle pressure of 10 g. The recorded images were deep black. The color images were superior in light resistance. The color change and discoloration when exposed to sunlight were not substantially appreciated.

EXAMPLE 95

6 g of 3-diethylamino-6-methyl-7-(p-biphenyl)aminofluoran obtained in Example 77 was dissolved in 40 ml of chloroform. 40 ml of 10% benzene solution of polystyrene and 5 g of carbon tetrabromide were added to the solution and the mixture was thoroughly stirred to prepare a coating composition. The coating composition was coated on polyethylene laminated paper having polyethylene at the both surfaces in the weight of 5 g/m$^2$ on dry basis in a dark place. The coated paper was irradiated with a light of eight ultraviolet lamps of 20 W from a distance of 5 cm for 10 minutes to develop black color images. The color images were then fixed by rinsing with a solution of acetone/n-hexane(1/5). The resultant images were stable when exposed to sunlight.

EXAMPLE 96

0.011 moles of 2-(2-hydroxy-4-pyrrolidino)benzoylbenzoic acid was reacted with 0.010 moles of 4-methoxy-4'-acetyldiphenylamine in 15 ml of concentrated sulfuric acid at room temperature for 24 hours. The obtained material was poured into 100 ml of ice-cold water and the aqueous system was adjusted to pH 11 by adding 20% aqueous solution of sodium hydroxide at room temperature. 50 ml of toluene was added to the aqueous system and the mixture was heated at 85° C. for 3 hours. The toluene layer was separated and the toluene was removed by vacuum distillation. The residue was recrystallized from ethyl alcohol to obtain 3-pyrrolidino-7-(p-acetylanilino)fluoran having melting point of 242°–244° C. in 89% yield. The fluoran derivative became black upon contact with silica gel.

EXAMPLE 97

0.01 moles of 2-[2-hydroxy-4-N-ethyl-N-(p-methylphenyl)amino]benzoylbenzoic acid was reacted with 0.01 moles of 4-ethoxy-4'-acetyldiphenylamine in 10 ml of concentrated sulfuric acid at room temperature for 24 hours. The obtained material was poured into 100 ml of ice-cold water and the aqueous system was adjusted to pH 12 by adding an aqueous solution of sodium hydroxide to produce a precipitate. The precipitate was filtered off and added to a mixture of 20 ml of benzene with 50 ml of an aqueous solution of sodium hydroxide having pH 12. The resultant mixture was refluxed for 3 hours and cooled on standing to produce crystals in the benzene layer. The crystals were filtered off and recrystallized from methyl alcohol to obtain 3-N-ethyl-N-(p-methylphenyl)amino-7-(p-acetylanilino)fluoran having a melting point of 273°–273.5° C. in 78% yield. The fluoran derivative became greenish black upon contact with silica gel.

EXAMPLE 98

0.01 moles of 2-(2-hydroxy-4-hexamethyleneimino)benzoylbenzoic acid was reacted with 0.01 moles of 2-methyl-4-ethoxy-3'-acetyldiphenylamine in 10 ml of concentrated sulfuric acid at room temperature for 24 hours. The obtained material was poured into 100 ml of ice-cold water and the aqueous system was adjusted to pH 11 by adding 20% aqueous solution of sodium hydroxide at room temperature. 30 ml of acetone was added to the system and the mixture was refluxed for 3 hours. The acetone was removed to produce a precipitate in the form of crystals. The precipitate was filtered off, washed with water and recrystallized from isopropyl alcohol to obtain 3-hexamethyleneimino-6-methyl-7-(m-acetylanilino)fluoran having a melting point of 189°–195° C. in 75% yield. The fluoran derivative became black upon contact with silica gel.

EXAMPLE 99

0.02 moles of 2-(2-hydroxy-4-N-methyl-N-cyclohexylamino)benzoylbenzoic acid was reacted with 0.01 moles of 3-methoxy-4-hydroxy-2'-benzoyl-diphenylamine in 30 ml of concentrated sulfuric acid at room temperature for 7 hours. The obtained material was poured into 100 ml of ice-cold water and the aqueous system was adjusted to pH 9 by adding 20% aqueous solution of sodium hydroxide at room temperature to produce a precipitate. The precipitate was filtered off, washed with water, dried and then recrystallized from benzene to obtain 3-N-methyl-N-cyclohexylamino-5-methoxy-7-(o-benzoylanilino)fluoran having a melting point of 178°–183° C. in 53% yield. The fluoran derivative became reddish black upon contact with silica gel.

EXAMPLES 100 TO 109

Example 96 was repeated to obtain various fluoran derivatives except that benzophenone derivatives shown in Table 8 was used instead of 2-(2-hydroxy-4-pyrrolidino)benzoic acid and that diphenylamine derivatives shown in Table 8 was used instead of 4-methoxy-4'-acetyldiphenylamine. The yield of the products and the colors formed upon contact with silica gel are shown in Table 8.

TABLE 8

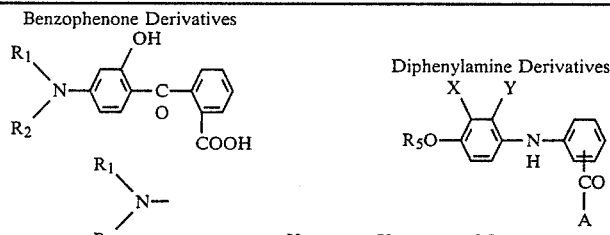

| Example No. | R$_1$, R$_2$ | X | Y | —CO—A | R$_5$ | Yield (%) | Developed Color |
|---|---|---|---|---|---|---|---|
| 100 | pyrrolidino | H | H | p-benzoyl | methyl | 91 | black |
| 101 | piperidino | H | H | p-acetyl | methyl | 85 | black |

TABLE 8-continued

Benzophenone Derivatives $R_1\diagdown$
$\phantom{R_1}N-$ [2-hydroxyphenyl with $-C(=O)-$ phenyl-COOH]
$R_2\diagup$ $R_1\diagdown$
$\phantom{R_1}N-$
$R_2\diagup$ Diphenylamine Derivatives $R_5O-$[phenyl with X, Y]$-N(H)-$phenyl$-CO-A$

| Example No. | R₁, R₂ | X | Y | —CO—A | R₅ | Yield (%) | Products Developed Color |
|---|---|---|---|---|---|---|---|
| 102 | pyrrolidino | H | H | p-propanoyl | ethyl | 89 | black |
| 103 | pyrrolidino | H | H | p-butanoyl | methyl | 88 | black |
| 104 | piperidino | H | H | p-benzoyl | ethyl | 80 | black |
| 105 | morpholino | H | ethyl | o-benzoyl | ethyl | 75 | reddish black |
| 106 | piperidino | t-butyl | H | p-acetyl | ethyl | 70 | black |
| 107 | pipelidino | H | methyl | p-benzoyl | ethyl | 73 | reddish black |
| 108 | N—ethyl-N—(p-chlorophenyl)amino | chlorine | H | p-(p-methylbenzoyl) | methyl | 55 | black |
| 109 | N—ethyl-N—(p-methylphenyl)amino | H | methyl | p-naphthoyl | methyl | 51 | reddish black |

EXAMPLE 110

A heat-sensitive record material was prepared in the same manner as in Example 17 except that 3-pyrrolidino-7-(p-acetylanilino)fluoran obtained in Example 96 was used instead of 3-diethylamino-6-methyl-7-α-naphthylaminofluoran.

The obtained record material which had a good white paper like appearance without fogging, was pressed with a pressure of 4 kg/cm² for 5 seconds on a plate heated at 125° C. to develop deep black images. The color images were superior in light resistance. The color change and discoloration when exposed to sunlight were not substantially appreciated.

Images were recorded on the record material with the use of a cylindrical scanning recording machine at a scanning speed of 0.7 m/sec with CO₂ gas laser (output: 1 W, beam diameter: 150 microns). Resultantly, deep black images were obtained.

EXAMPLE 111

A pressure-sensitive record material was prepared in the same manner as in Example 18 except that fluoran derivative obtained in Example 96 was used instead of fluoran derivative obtained in Example 1.

Several of the pressure-sensitive record material were piled in the manner as the capsule coated layer was closed to the acceptor coated layer, pressed with driving a pen to obtain black color images on the acceptor coated surface. The color images were obtained with a rapid color development and in a deep color immediately after press, and the color change and discoloration were not appreciated when exposed to sunlight.

EXAMPLE 112

200 parts of cuprous iodide and 5 parts of 10% aqueous solution of sodium sulfite were added to 200 parts of 1% aqueous solution of polyvinyl alcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m² in the weight of 7 g/m² on dry basis. Further, there was coated on the coating layer in the weight of 5 g/m² on dry basis a heat-sensitive coating composition prepared by the same manner as in Example 110 except that 3-N-ethyl-N-(p-methylphenyl)amino-7-(p-acetylanilino)fluoran obtained in Example 97 was used instead of 3-pyrrolidino-7-(p-acetylanilino)fluoran to obtain an electrothermal record material.

Images were recorded on the record material with the use of a cylindrical scanning recording machine at a scanning speed of 630 mm/sec with a needle pressure of 10 g. The recorded images were dark greenish black. The color images were superior in light resistance. The color change and discoloration when exposed to sunlight were not substantially appreciated.

EXAMPLE 113

6 g of 3-N-ethyl-N-(p-methylphenyl)amino-7-(p-acetylanilino)fluoran obtained in Example 97 was dissolved in 40 ml of chloroform. 40 ml of 10% benzene solution of polystyrene and 5 g of carbon tetrabromide were added to the solution and the mixture was thoroughly stirred to prepare a coating composition. The coating composition was coated on polyethylene laminated paper having polyethylene at the both surfaces in the weight of 5 g/m² on dry basis in a dark place. The coated paper was irradiated with a light of eight ultraviolet lamps of 20 W from a distance of 5 cm for 10 minutes to develop black color images. The color images were then fixed by rinsing with a solution of acetone/n-hexane(1/5). The resultant images were stable when exposed to sunlight.

EXAMPLE 114

0.011 moles of 2-(2-hydroxy-4-diethylamino)benzoylbenzoic acid was reacted with 0.010 moles of 4-methoxy-4'-trifluoromethyldiphenylamine in 15 ml of concentrated sulfuric acid at room temperature for 24 hours. The obtained material was poured into 100 ml of ice-cold water and the aqueous system was adjusted to pH 11 by adding 20% aqueous solution of sodium hydroxide at room temperature. 50 ml of toluene was added to the system and then the mixture was heated at 85° C. for 3 hours. The toluene layer was separated and the toluene was removed by vacuum distillation. The residue was recrystallized from ethyl alcohol to obtain 3-diethylamino-7-(p-trifluoromethylanilino)fluoran as colorless crystals in the form of needles in 83% yield. The fluoran derivative had a melting point of 194°–195° C. and became black upon contact with silica gel.

EXAMPLE 115

0.01 moles of 2-(2-hydroxy-4-dimethylamino)benzoylbenzoic acid was reacted with 0.01 moles of 4-hydroxy-2'-trifluoromethyldiphenylamine in 10 ml of concentrated sulfuric acid at room temperature for 7 hours. The obtained material was poured into 100 ml of ice-cold water and the aqueous system was adjusted to pH 9 by adding 20% aqueous solution of sodium hydroxide at room temperature. The produced precipitate was filtered off, washed with water, dried and then recrystallized from benzene to obtain 3-dimethylamino-7-(o-trifluoromethylanilino)fluoran as colorless crystals in 56% yield. The fluoran derivative had a melting point of 183°–186° C. and became black upon contact with silica gel.

EXAMPLE 116

0.01 moles of 2-(2-hydroxy-4-dibutylamino)benzoylbenzoic acid was reacted with 0.01 moles of 2-methyl-4-ethoxy-4'-trifluoromethyldiphenylamine in 10 ml of concentrated sulfuric acid at room temperature for 24 hours. The obtained material was poured into 100 ml of ice-cold water and the aqueous solution was adjusted to pH 11 by adding 20% aqueous solution of sodium hydroxide at room temperature. 30 ml of acetone was added to the system and the mixture was refluxed for 3 hours. Then acetone was removed to obtain a precipitate in the form of crystals. The precipitate was filtered off, washed with water and recrystallized from isopropyl alcohol to obtain 3-dibutylamino-6-methyl-7-(p-trifluoromethylanilino)fluoran as colorless crystals in the form of needles in 71% yield. The fluoran derivative had a melting point of 156°–159° C. and became reddish black upon contact with silica gel.

EXAMPLE 117

A heat-sensitive record material was prepared in the same manner as in Example 17 except that 3-diethylamino-7-(p-trifluoromethylanilino)fluoran obtained in Example 114 was used instead of 3-diethylamino-6-methyl-7-α-naphthylaminofluoran.

The obtained record material which had a good white paper like appearance without fogging, was pressed with a pressure of 4 kg/cm$^2$ for 5 seconds on a plate heated at 125° C. to develop deep black images. The color images were superior in light resistance. The color change and discoloration when exposed to sunlight were not substantially appreciated.

Images were recorded on the record material with the use of a cylindrical scanning recording machine at a scanning speed of 0.7 m/sec with CO$_2$ gas laser (output: 1 W, beam diameter: 150 microns). Resultantly, deep black images were obtained.

EXAMPLE 118

A pressure-sensitive record material was prepared in the same manner as in Example 18 except that fluoran derivative obtained in Example 114 was used instead of fluoran derivative obtained in Example 1.

Several of the pressure-sensitive record material were piled in the manner as the capsule coated layer was closed to the acceptor coated layer, pressed with driving a pen to obtain dark greenish black color images on the acceptor coated surface. The color images were obtained with a rapid color development and in a deep color immediately after press, and the color change and discoloration were not appreciated when exposed to sunlight.

EXAMPLE 119

200 parts of cuprous iodide and 5 parts of 10% aqueous solution of sodium sulfite were added to 200 parts of 1% aqueous solution of polyvinyl alcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m$^2$ in the weight of 7 g/m$^2$ on dry basis. Further, there was coated on the coating layer in the weight of 5 g/m$^2$ on dry basis a heat-sensitive coating composition prepared by the same manner as in Example 117 except that 3-dimethylamino-7-(o-trifluoromethylanilino)fluoran obtained in Example 115 was used instead of 3-diethylamino-7-(p-trifluoromethylanilino)fluoran to obtain an electrothermal record material.

Images were recorded on the record material with the use of a cylindrical scanning recording machine at a scanning speed of 630 mm/sec with a needle pressure of 10 g. The recorded images were deep black. The color images were superior in light resistance. The color change and discoloration when exposed to sunlight were not substantially appreciated.

EXAMPLE 120

6 g of 3-dibutylamino-6-methyl-7-(p-trifluoromethylanilino)fluoran obtained in Example 116 was dissolved in 40 ml of chloroform. 40 ml of 10% benzene solution of polystyrene and 5 g of carbon tetrabromide were added to the solution and the mixture was thoroughly stirred to prepare a coating composition. The coating composition was coated on polyethylene laminated paper having polyethylene at the both surfaces in the weight of 5 g/m$^2$ on dry basis in a dark place. The coated paper was irradiated with a light of eight ultraviolet lamps of 20 W from a distance of 5 cm for 10 minutes to develop reddish black color images. The color images were then fixed by rinsing with a solution of acetone/n-hexane(1/5). The resultant images were stable when exposed to sunlight.

What we claim is:

1. A recording system which utilizes the color forming reaction between a colorless chromogenic material an electron accepting acidic reactant material, characterized in that said colorless chromogenic material comprises at least one fluoran derivative having the general formula:

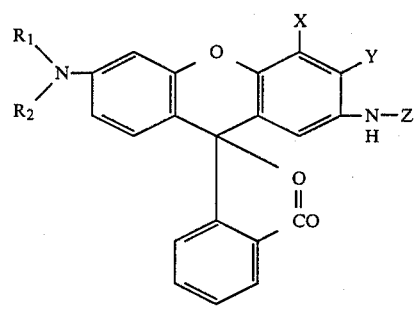

wherein Z is —CH$_2$COOCH$_2$CH=CH$_2$,

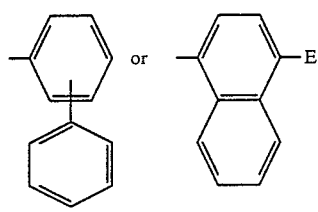 or 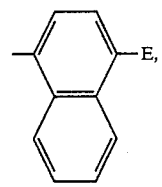

wherein E is hydrogen or

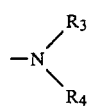

wherein each $R_3$ and $R_4$ is hydrogen, an alkyl having 1 to 4 carbon atoms or phenyl;
each $R_1$ and $R_2$ is an alkyl having 1 to 12 carbon atoms or an aralkyl having 7 to 9 carbon atoms; X is hydrogen, halogen atom, an alkyl having 1 to 4 carbon atoms or an alkoxyl having 1 to 2 carbon atoms; and Y is hydrogen, halogen atom or an alkyl having 1 to 4 carbon atoms; however,
when Z is

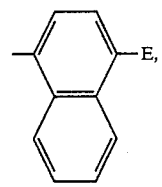

at least one of X and Y is selected from the before-mentioned substituents other than hydrogen.

2. A recording system according to claim 1, in which said recording system is a pressure-sensitive recording system.

3. A recording system according to claim 1, in which said recording system is a heat-sensitive recording system.

* * * * *